United States Patent
Recanati et al.

(10) Patent No.: US 11,096,626 B2
(45) Date of Patent: Aug. 24, 2021

(54) FETAL SCALP MONITOR

(71) Applicants: Maurice-Andre Recanati, New York, NY (US); Katherine J. Kramer, Philadelphia, PA (US); Robert Alan Welch, West Bloomfield, MI (US); Sorin Draghici, Ann Arbor, MI (US); Maik Huttemann, Grosse Pointe, MI (US); Kelin Prokurat, Detroit, MI (US); Mohammad Ali E. Ozbeki, Novi, MI (US)

(72) Inventors: Maurice-Andre Recanati, New York, NY (US); Katherine J. Kramer, Philadelphia, PA (US); Robert Alan Welch, West Bloomfield, MI (US); Sorin Draghici, Ann Arbor, MI (US); Maik Huttemann, Grosse Pointe, MI (US); Kelin Prokurat, Detroit, MI (US); Mohammad Ali E. Ozbeki, Novi, MI (US)

( * ) Notice: Subject to any disclaimer, the term of this patent is extended or adjusted under 35 U.S.C. 154(b) by 238 days.

(21) Appl. No.: 15/985,884

(22) Filed: May 22, 2018

(65) Prior Publication Data

US 2018/0333099 A1     Nov. 22, 2018

Related U.S. Application Data

(60) Provisional application No. 62/509,728, filed on May 22, 2017.

(51) Int. Cl.
*A61B 5/00* (2006.01)
*A61B 5/1464* (2006.01)
*A61B 5/0205* (2006.01)

(52) U.S. Cl.
CPC ............ *A61B 5/688* (2013.01); *A61B 5/0011* (2013.01); *A61B 5/02055* (2013.01);
(Continued)

(58) Field of Classification Search
CPC ..... A61B 5/688; A61B 5/0011; A61B 5/0448; A61B 8/02; A61B 5/02055; A61B 5/1464;
(Continued)

(56) References Cited

U.S. PATENT DOCUMENTS

| | | | | |
|---|---|---|---|---|
| 4,209,020 A | * | 6/1980 | Nielsen | A61B 5/0416 600/376 |
| 4,281,659 A | * | 8/1981 | Farrar | A61B 5/0448 204/403.02 |

(Continued)

*Primary Examiner* — Ankit D Tejani
*Assistant Examiner* — Joshua Brendon Solomon
(74) *Attorney, Agent, or Firm* — Jacob M. Ward; Ward Law Office LLC (57) ABSTRACT

A fetal scalp monitor is disclosed that enables a medical professional to monitor the well-being of a fetus in utero. The fetal scalp monitor has a main body, with a central core having a temperature sensor, conductive dome, grounding ring, and tocodynamometer. The main body also has at least one adhesive portion to facilitate the attachment of the device onto the scalp of a fetus, and a plurality of concentric rings to militate against amniotic fluids from entering the adhesive portion. The vital signs of the infant and conditions inside the uterus are then transmitted, either wired or wirelessly, to a fetus monitoring device.

20 Claims, 6 Drawing Sheets

(52) U.S. Cl.
CPC .......... *A61B 5/1464* (2013.01); *A61B 5/4362* (2013.01); *A61B 5/6814* (2013.01); *A61B 2503/02* (2013.01); *A61B 2562/16* (2013.01)

(58) Field of Classification Search
CPC . A61B 5/4362; A61B 5/6814; A61B 2503/02; A61B 2562/16; A61F 2/0063
See application file for complete search history.

(56) References Cited

U.S. PATENT DOCUMENTS

| | | | |
|---|---|---|---|
| 4,308,873 A * | 1/1982 | Maynard | A61B 5/04004 600/378 |
| 4,488,558 A * | 12/1984 | Simbruner | A61B 5/02055 600/376 |
| 5,442,940 A * | 8/1995 | Seeker | A61B 8/02 600/453 |
| 5,529,064 A | 6/1996 | Rall et al. | |
| 5,551,424 A | 9/1996 | Morrison et al. | |
| 5,833,622 A * | 11/1998 | Meathrel | A61B 5/04087 600/511 |
| 7,818,050 B2 * | 10/2010 | Rapoport | A61B 5/0444 600/511 |
| 8,600,473 B2 | 12/2013 | Gingsjo | |
| 2002/0068852 A1 * | 6/2002 | Coakley | A61B 1/00177 600/160 |
| 2003/0103877 A1 * | 6/2003 | Long | H01J 37/32009 422/186.04 |
| 2007/0198027 A1 * | 8/2007 | Morch | A61B 17/442 606/123 |
| 2010/0256482 A1 * | 10/2010 | Peters | A61M 16/0486 600/424 |
| 2013/0060259 A1 * | 3/2013 | Porat | A61B 5/0011 606/123 |
| 2013/0096440 A1 * | 4/2013 | Kiraly | A61B 8/02 600/483 |
| 2014/0025093 A1 * | 1/2014 | Horton | A61F 2/0063 606/151 |
| 2015/0142090 A1 * | 5/2015 | Duijsens | A61N 1/05 607/116 |
| 2017/0367643 A1 * | 12/2017 | Falk | A61B 8/488 |
| 2018/0206886 A1 * | 7/2018 | Beaven | A61B 17/442 |
| 2019/0192027 A1 * | 6/2019 | Wohlschlager | A61B 5/0011 |

* cited by examiner

FETAL SCALP MONITOR

CROSS REFERENCE TO EARLIER APPLICATIONS

This application claims the benefit of U.S. Provisional Patent Application Ser. No. 62/509,728, filed on May 22, 2017. The entire disclosure of the above application is hereby incorporated herein by reference.

FIELD

The present disclosure relates to a medical device and, more specifically, to an atraumatic fetal scalp monitor or sensor for electronic fetal heart, temperature, or tocometric monitoring.

BACKGROUND

Electronic cardiotocography was invented decades ago as a means of assessing fetal well-being during labor with the goal of decreasing morbidity and mortality both in the mother and in the baby. Since intrapartum hypoxia leads to changes in the fetal heart rate and, in prolonged or severe cases, to permanent neurological damage or death of the baby, fetal monitoring has become the standard of care in the modern delivery room. While fetal heart monitoring typically utilizes ultra-sonographic waves to record the baby's heart rate, there are instances, such as maternal obesity and the baby being poorly positioned or behind the pubic bone, that this modality cannot be used reliably. In these scenarios a fetal scalp electrode may be used.

Conventional fetal scalp electrodes typically include a piece of metal that is shaped like a corkscrew. This screw pierces the skin on the head of the fetus to provide an electrical and mechanical attachment with the fetus. However, this has been found to be traumatic for the fetus and is undesirable. The use of the screw may lead to scalp abscesses in the head of the fetus. The screw also cannot be used when the fetus is younger than 34 weeks or when the mother is infected with hepatitis or human immunodeficiency virus (HIV).

These conventional fetal scalp electrodes are described, for example, in U.S. Pat. No. 8,600,473 to Gingsjo, which describes that the electrode is attached to the fetal scalp using a screw, and U.S. Pat. No. 5,551,424 to Morrison, which describes metal leads that extend into fetal tissue. In another example, U.S. Pat. No. 5,529,064 issued to Rall describes a dome like cup that is reliant upon penetrating fetal skin. However, any device that penetrates the skin of a fetus is undesirably invasive and may create a portal of entry for viruses to infect the fetus.

If there is an infection during pregnancy, the fetus may develop a fever. Monitoring the temperature of the fetus for early signs of infection, such as chorioamnionitis, is important when managing patients who have been in labor for an extended period of time. Currently, the common practice among experienced clinicians is to insert a hand into the uterine cavity to feel for changes in temperature. Measuring the precise temperature of the fetus would also offer medical professionals invaluable clinical data in preventing infection.

During the birthing process, it may also be necessary to measure the force of the contractions. The timing of changes in the fetal heart rate, when correlated with the timing of the onset of uterine contractions, helps medical professionals evaluate the well-being of the fetus during labor. For these reasons, in certain circumstances, having tocometry data may become crucial in managing patient safely.

There is need for a fetal scalp monitor that can detect the fetal heart rate, body temperature, and the force of contractions within the uterus, without causing trauma to the fetus.

SUMMARY

In concordance with the instant disclosure, a fetal scalp monitor that can monitor the fetal heart rate, body temperature, and the force of contractions within the uterus, without causing trauma to the fetus, has been surprisingly discovered.

In one embodiment, the fetal scalp monitor has a substantially flat, thin, circular main body, with no separable parts. The fetal scalp monitor has a central core, with a conductive dome in electrical contact with the fetal skin and electrically isolated from the maternal (uterine) environment, and a temperature sensor in contact with the fetal skin. The inner surface of the conductive dome is slightly convex, with a volume of electrolyte gel ensuring contact between the conductive dome and the fetal skin. The gel allows for rapid temperature equilibration between the fetal skin and the temperature sensor. The thin plastic backbone is electrically shielded from the conductive dome by an additional insulating layer, which is of a greater diameter than the conductive dome. The thin plastic backbone also has an area allowing insulated wires to exit the fetal scalp monitor.

In a further embodiment, there are concentric adhesive areas around the central core, containing a biocompatible adhesive, capable of securely attaching to the fetal skin in wet/damp conditions. The adhesive is easily removable without damaging the fetal skin's integrity, and is located radially outwardly from the inner ring. The main body has two separate rings of biocompatible adhesive, with an intermediate ring separating a first adhesive portion and a second adhesive portion. The main body has an outer ring surrounding the second adhesive portion. Connecting the intermediate ring and outer ring is a plurality of radial walls further separating the second adhesive portion into independent compartments.

In another embodiment, the main body is a thin, flexible, waterproof plastic backbone, which begins from the center of the generally circular device and extends a short distance beyond an outer ring. The main body is constructed of a thin and pliable material, an electrically isolating material, a waterproof material, a biocompatible material, and a material which is sterilized. Additionally, the main body has grooves molded or etched on its inner surface to support an inner ring, intermediate ring, and outer ring. The main body has a thin removable peel-off backing, extending from the center of the fetal scalp monitor to beyond the edge of the plastic backbone, constructed of a material loosely adherent to the biocompatible adhesive, preventing desiccation of the adhesive and the electrolyte gel. Furthermore, a grounding ring is located on the second side of the plastic backbone and is made of a conductive material capable of providing the grounding electric potential of the maternal (uterine) environment. The main body also has a groove molded or etched on its second side to accommodate the grounding ring.

In an additional embodiment, there are a plurality of wires are electrically and mechanically connected to the temperature sensor, the thin conductive dome, and the grounding ring. There is a plastic plug terminating at the distal end of the wires, which is compatible with standard electronic fetal monitoring devices. The wires connect to the monitoring devices either directly, or through an adapter. In certain embodiments, the main body has a strap that allows the physician to introduce two fingers between the device and the strap.

In certain embodiments, the fetal scalp monitor has an integrated tocodynamometer ring utilized to measure pressure on the second side of the fetal scalp monitor located concentrically outside from the grounding ring. The tocodynamometer ring contains an electronic force transducer and an insulated electric wire exiting from it. In another embodiment, the tocodynamometer ring is filled with a fluid to measure pressure and has a tube for relaying pressure changes existing from it instead of an insulated electric wire. The tocodynamometer is compatible with the standard electronic fetal monitoring equipment either directly or through an adapter.

In a particular embodiment, the fetal scalp monitor has no sharp angles, and is securely attached to the fetus through the birth canal. The fetal scalp monitor is easy to apply to the fetus, and can easily be removed without injuring the fetus. The fetal scalp monitor has a low electrical resistance connection with the fetus. The fetal scalp monitor allows the fetus' temperature to be monitored in a continuous fashion. Furthermore, the fetal scalp monitor is substantially flat and will not interfere with the fetus' movements through the birth canal. The fetal scalp monitor can monitor the fetal heart rate, the fetal temperature and the tocometric pressure continuously and simultaneously. The fetal scalp monitor is also capable of wireless data transmission and would not have any wires or tubes exiting the mother to the fetal scalp monitor.

In an additional embodiment, the fetal scalp monitor has a main body with a first side and a second side. The first side of the fetal scalp monitor has an electrical ground, while the second side has a conductive dome, a temperature sensor, a plurality of concentric rings, and at least one adhesive portion.

In another embodiment, the fetal scalp monitor has a main body with a first and second side. The first side of the fetal scalp monitor has a grounding ring. The second side of the fetal scalp monitor has a conductive dome, a temperature sensor, and an inner ring, wherein a gel surrounds the conductive dome and the temperature sensor. The second side also has an intermediate ring and an outer ring, both surrounding the inner ring. A first adhesive portion is disposed between the inner ring and the intermediate ring, and a second adhesive portion is disposed between the intermediate ring and the outer ring. The temperature sensor, the conductive dome, and the grounding ring are each configured to be in communication with a fetal monitoring device.

In further embodiment, there is a method for attaching a fetal scalp monitor to a fetal scalp. The first step is to provide a main body with a first side and a second side. The first side having an electrical ground, and the second side having a conductive dome, a temperature sensor, a plurality of concentric rings, and at least one adhesive portion. The second step involves inserting the device into the birth canal and pressing the main body onto the scalp of a fetus until the main body is adhered to the fetal scalp.

DRAWINGS

The above, as well as other advantages of the present disclosure, will become clear to those skilled in the art from the following detailed description, particularly when considered in the light of the drawings described hereafter.

DETAILED DESCRIPTION

The following detailed description and appended drawings describe and illustrate various embodiments of the fetal scalp monitor. The description and drawings serve to enable one skilled in the art to make and use the fetal scalp monitor, and are not intended to limit the scope of the fetal scalp monitor in any manner. In respect of the methods disclosed, the steps presented are exemplary in nature, and thus, the order of the steps is not necessary or critical unless otherwise disclosed.

Figure 1:
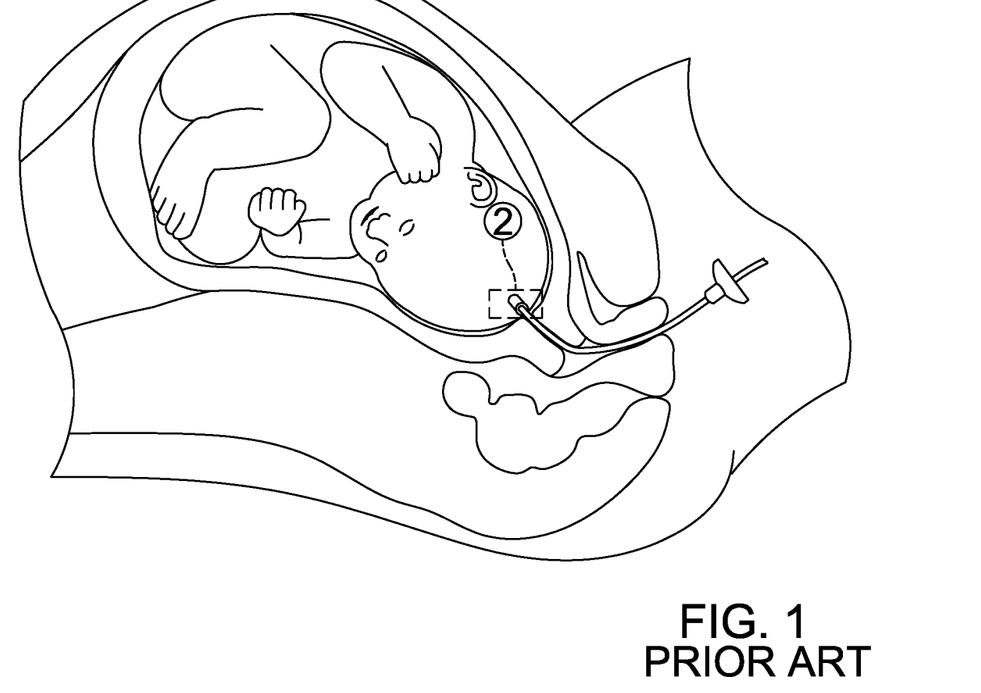
FIG. 1 is a prior art illustration of a fetal scalp monitor having a screw attached to the scalp of a fetus in utero.
Figure 2:
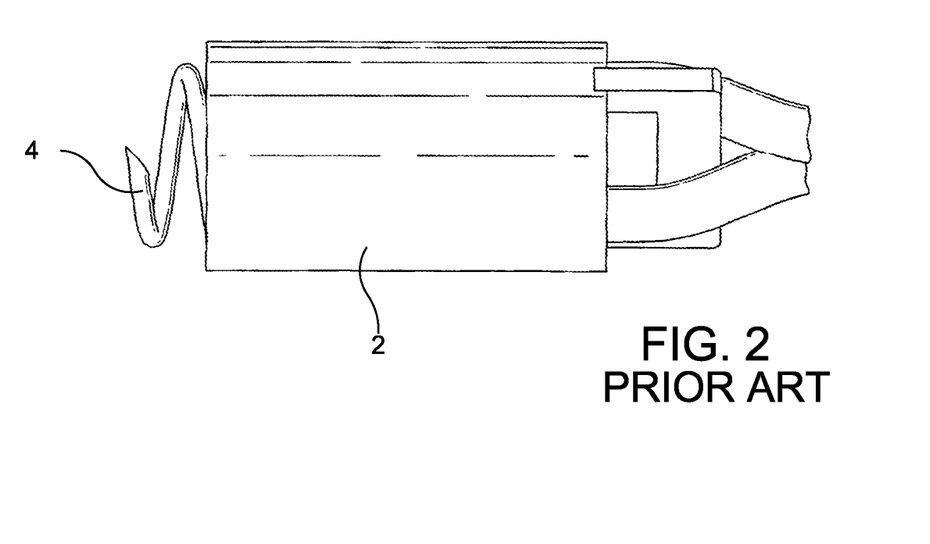
FIG. 2 is a prior art illustration of the fetal scalp monitor taken at call-out 2 in FIG. 1.

For purpose of comparison, a fetal scalp monitor or electrode of the prior art is shown in FIGS. 1-2. The main body 2 of the conventional fetal scalp monitor attaches to the fetal scalp using a screw 4, which pierces the skin on the head to provide an electrical and mechanical attachment with the fetus 1. Attaching the main body 2 of the fetal scalp monitor using a screw 4 is invasive and can cause infection, bleeding, and cannot be used when the fetus 1 is younger than 34 weeks, or when the mother is infected with hepatitis or human immunodeficiency virus.

In contrast, a fetal scalp monitor 100 of the present disclosure is configured to atraumatically adhere to a fetus 101 in utero without the need to pierce the scalp of the fetus 101 to receive relevant data. The fetal scalp monitor 100, illustrated in FIGS. 3-8, may be used to simultaneously and continuously monitor the fetal heart rate, the fetal body temperature and, in certain embodiments, the force of contractions within the uterus. Advantageously, these parameters are measured in a non-invasive manner that is safe for both the mother and the fetus 101. The fetal scalp monitor 100 may be sterilized, disposable, inexpensive to manufacture, and suitable for placement within the human body. The fetal scalp monitor 100 is capable of securely attaching to the fetus 101 in an atraumatic manner through the birth canal.

The fetal scalp monitor 100 has a main body 102 with a first side 104 and a second side 106. The main body 102 of the fetal scalp monitor has a thin flexible backbone 108. The back bone 108 may be a polycarbonate, a polyethylene, a polypropylene, or any other bio-compatible material chosen by a skilled artisan, as desired. In particular embodiments, the main body 102 and back bone may be formed by an injection molding process, although other suitable process may also be employed. In certain embodiments, the diameter of the main body 102 is between 1.5 cm and 4.0 cm, although other suitable dimensions may also be employed.

The first side 104 of the main body 102 is configured to monitor conditions in the uterus and transmit the data collected to a fetal monitoring device (not shown), while the second side 106 is configured to contact the skin on the scalp of the fetus 101 and monitor vital signs.

Figure 4:
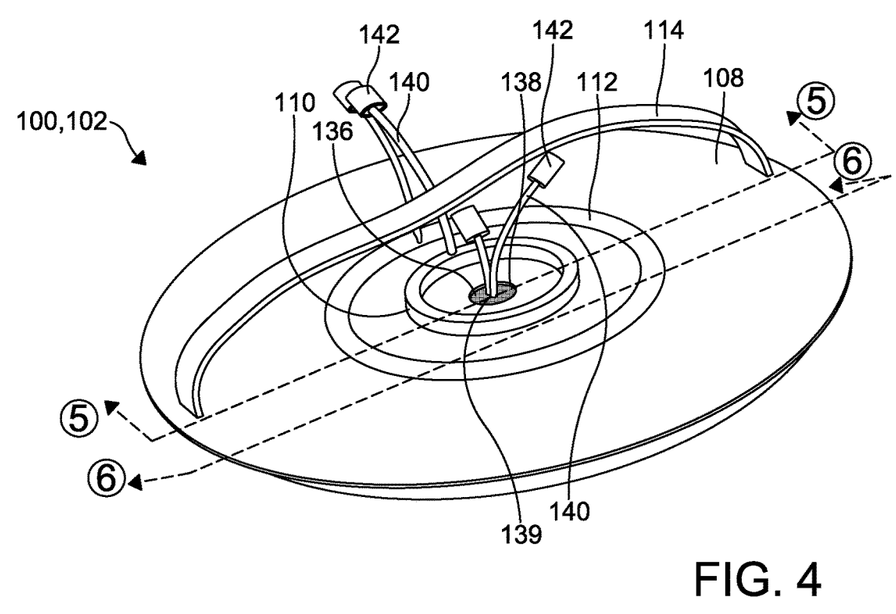
FIG. 4 is a top perspective view of the fetal scalp monitor taken at call-out 4 in FIG. 3.

FIG. 4 illustrates the first side 104 of the main body 102. The first side 104 of the main body 102 has a grounding ring 110. The ground ring 110 is configured to provide a grounding electric potential of the uterine environment at every moment in time. In certain embodiments, the second side 106 may also have a tocodynamometer ring 112. The tocodynamometer ring 112 is disposed concentrically outside of the grounding ring 110. The tocodynamometer ring 112 is configured to measure the pressure within the uterine environment. In certain examples, the tocodynamometer ring 112 may contain an electronic force transducer, or may be filled with fluid and have a protruding hollow tube that is configured to connect with the fetal monitoring device. Although the tocodynamometer 112 and electrical ground 110 are shown as rings, they may be any suitable shape as chosen by a skilled artisan.

The first side 104 of the main body 102 may further have a strap 114. The strap 114 is configured to accommodate a physician's fingers, e.g., it may have enough slack to accommodate the index and middle fingers of the physician, so that the physician may secure place the fetal scalp monitor 100. In particular, the strap 114 may be attached to the first side 104 to facilitate the attachment of the fetal scalp monitor onto the fetus 101. The flexible backbone 108 may also be molded with indents, grooves, or recesses on the first side 104 that are configured to receive the grounding ring 110 and tocodynamometer ring 112, as desired.

As shown in FIGS. 5-8, the second side 106 of the main body 102 may have a central core 115 with a conductive dome 118 surrounding a sensor 120. As a non-limiting example, the sensor 120 may be a temperature sensor and is described herein as such; however, it should be appreciated that the sensor 120 may be configured to measure other parameters, as desired. For example, the temperature sensor 120 may be a thermocouple, or any other suitable type of temperature sensor 120 that may be chosen by a skilled artisan.

The conductive dome 118 is configured to monitor fetal vital signs, such as heart rate and blood pressure, as non-limiting examples. The conductive dome 118 may be formed of any conductive material suitable for use in utero as may be selected by one of ordinary skill in the art. For example, the conductive dome 118 may be a metal with high conductance and low resistance such as copper or aluminum. The dome 118 is also a thin foil, having a thickness foil of about 0.016 mm (0.63 mils) to about 0.024 mm (0.94 mils), as a nonlimiting example. The shape of the dome 118 may be formed by a stamping process. One of ordinary skill in the art may also elect other suitable conductive materials, dimensions, and method of formation, as desired.

Figure 5:
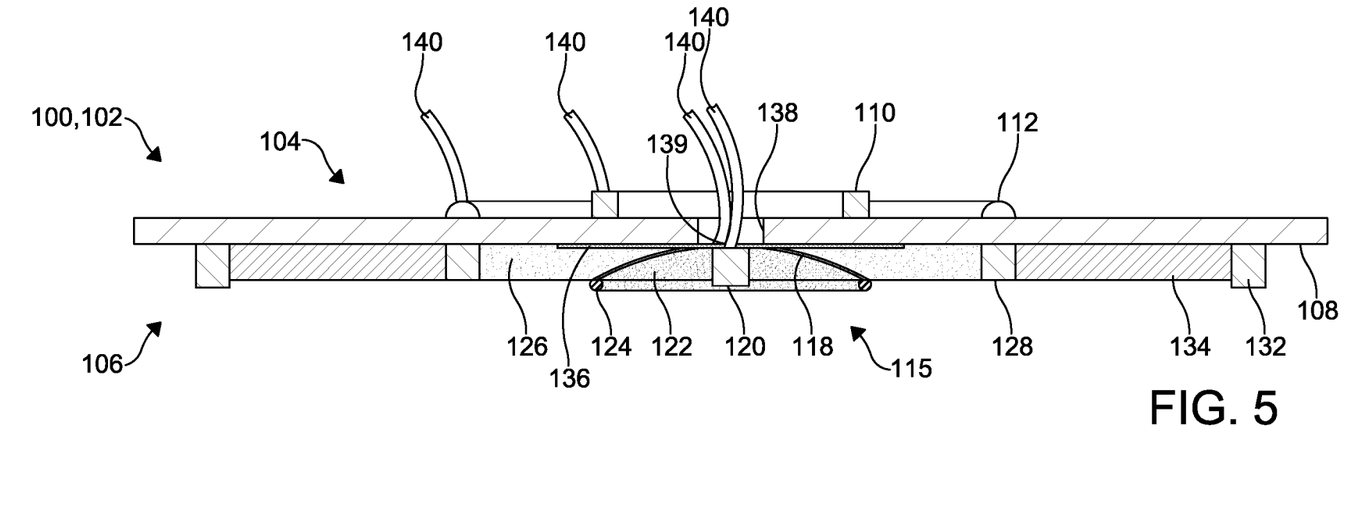
FIG. 5 is a cross-sectional, side elevational view of the fetal scalp monitor taken at section line 5 in FIG. 4.
Figure 6:
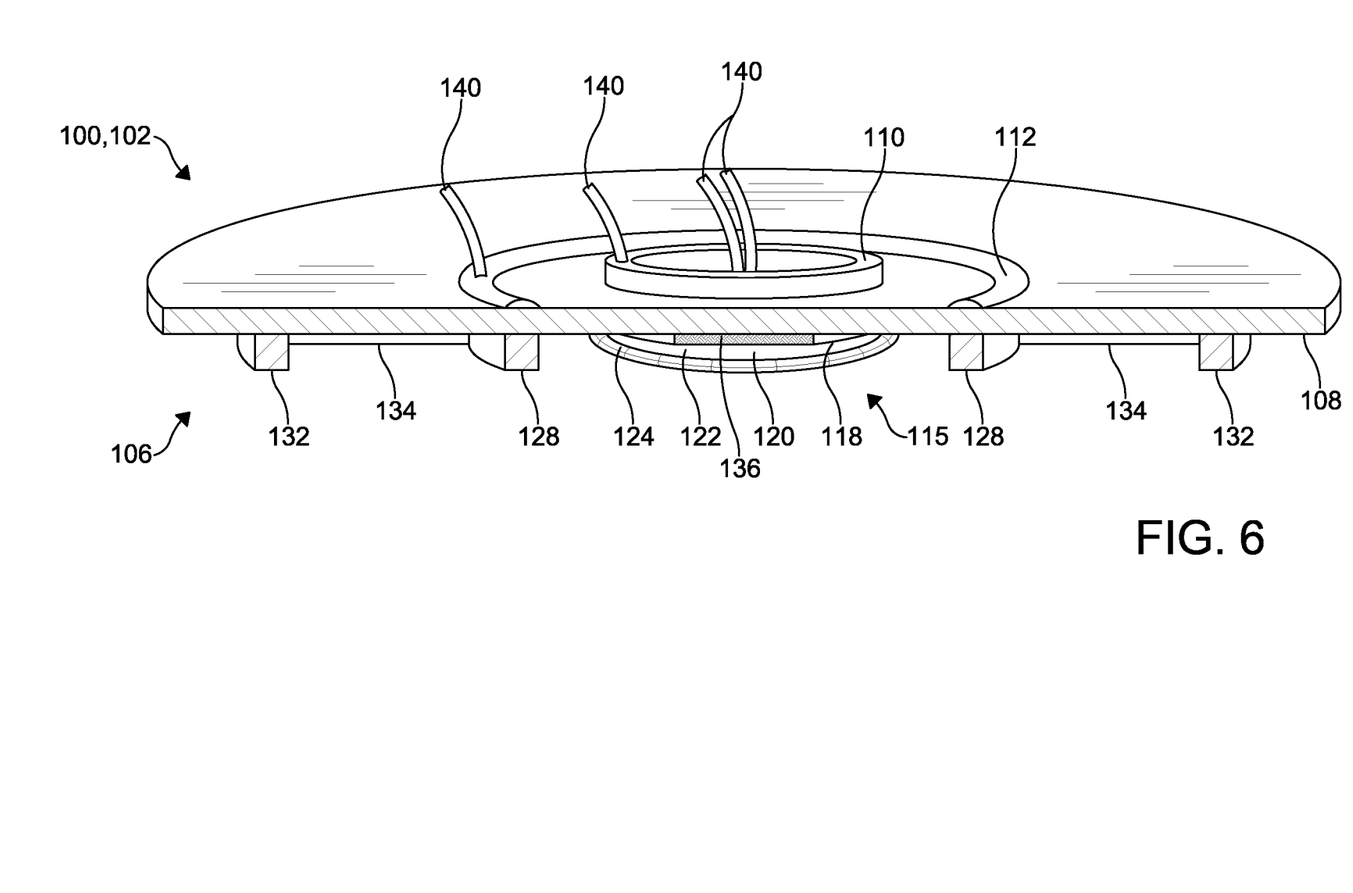
FIG. 6 is a cross-sectional, top perspective view of the fetal scalp monitor taken at section line 6 in FIG. 4, shown without an adhesive and an electrolyte gel for purpose of illustration.
Figure 8:
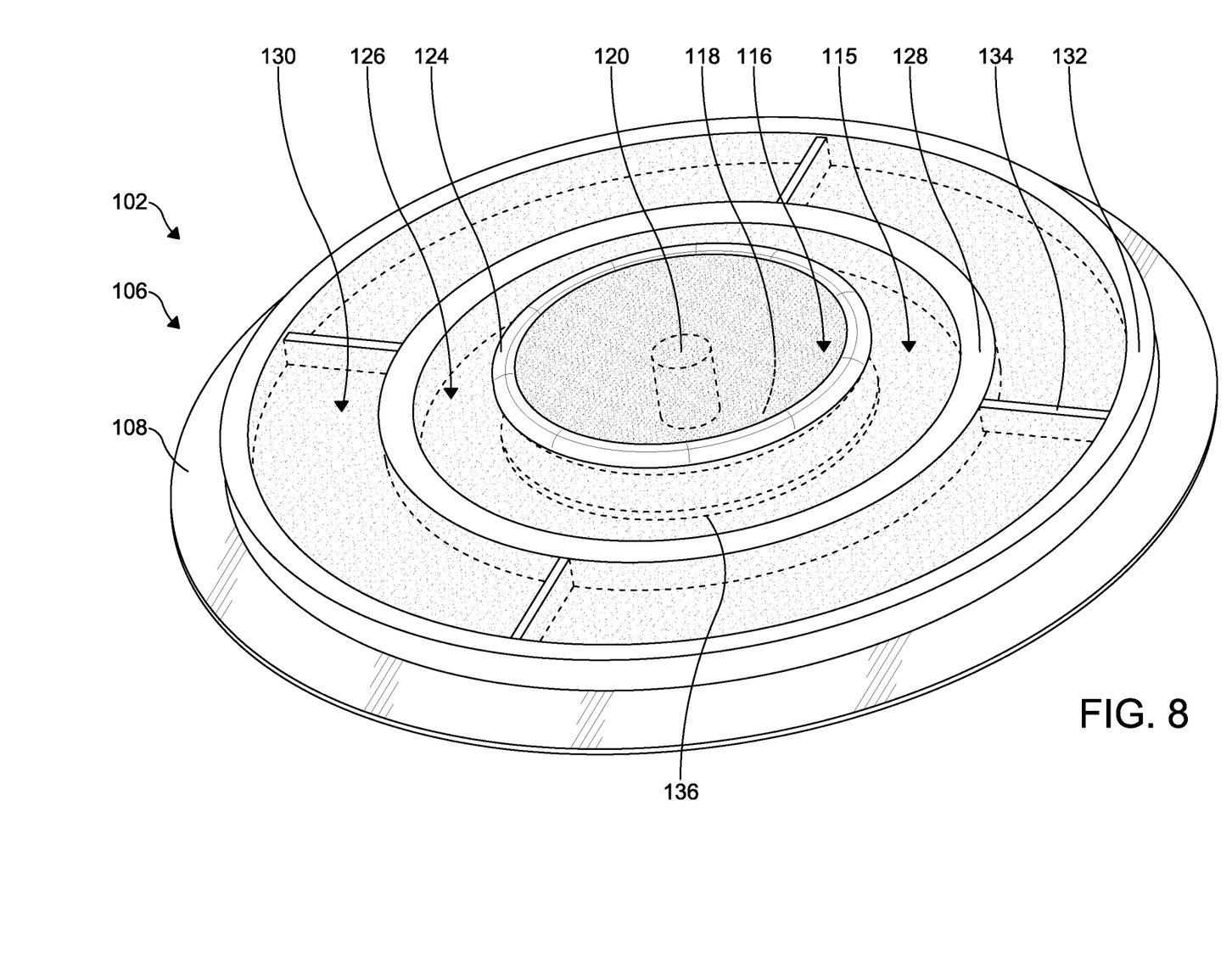
FIG. 8 is a bottom perspective view of the fetal scalp monitor of FIG. 3, shown with the adhesive and the electrolyte gel and ready for use.

To improve the accuracy of the readings, the conductive dome 118 and temperature sensor 120 are at least partly covered in an electrolyte gel 116 that is disposed within the cavity of the conductive dome 118, as shown in FIGS. 5 and 8. The electrolyte gel 116 advantageously provides for electrical communication between the conductive dome 118 and the scalp of the fetus by the electrolyte gel 116 contacting the fetus 101, even when the conductive material of the dome 118 is not otherwise in contact with the fetus 101. Non-limiting examples of suitable electrolyte gels 116 are described in U.S. Pat. No. 5,800,685 to Perrault. Other suitable types of electrolyte gels 116 may also be employed within the scope of the present disclosure.

Figure 7:
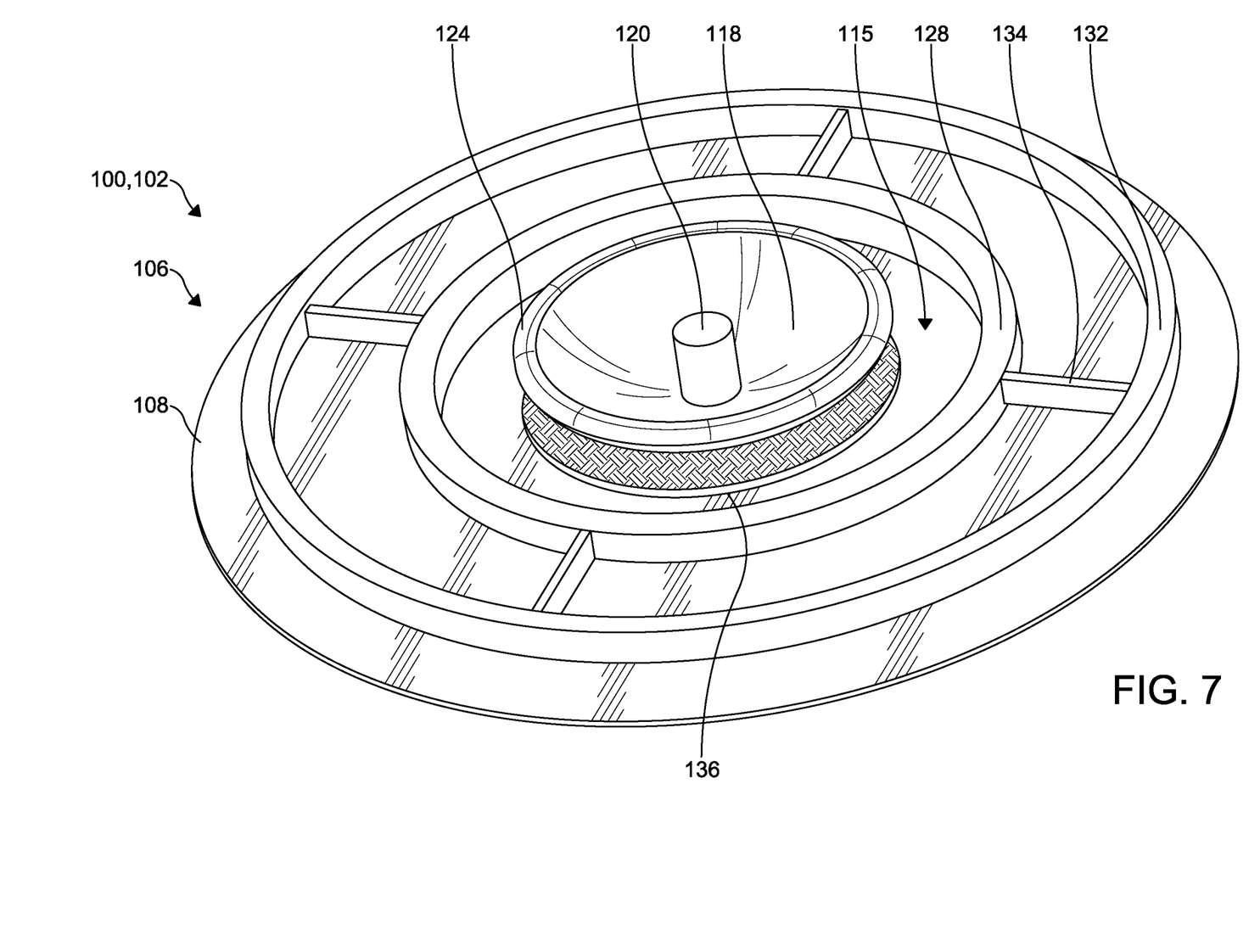
FIG. 7 is a bottom perspective view of the fetal scalp monitor of FIG. 3, shown without the adhesive and the electrolyte gel for purpose of illustration.

Illustrated in FIG. 7, an inner ring 124 is further affixed to the top or free edge of the conductive dome 118. When the second side 106 is in contact with the fetal scalp, the inner ring 124 acts as a barrier against a leakage of the electrolyte gel 116 outside of the conductive dome 118, in order to keep the conductive dome 118 and the temperature sensor 120 bathed in electrolyte gel 116. The inner ring 124 may be formed from an elastomer, for example, suitable for forming a seal with the fetal scalp. The elastomer may be either electrically conductive or non-conductive, as desired.

As mentioned, the electrolyte gel 116 ensures consistent electric contact between the conductive dome 118 and the fetal skin. It may also be adapted to effectively transmit heat from the fetus 101 to the temperature sensor 120. The conductive dome 118 is also slightly convex in shape to include a sufficient amount of electrolyte gel 116. The sufficient amount of electrolyte gel 116 provides for increased conductivity between the fetal scalp and the conductive dome 118. The type of electrolyte gel 116 can be any gel suitable for use in utero as chosen by a skilled artisan, including but not limited to covidien conductive adhesive hydrogels, gels made from acrylic esters of quaternary chlorides and/or sulfates or acrylic amides of quaternary chlorides, and gels formed of glucose chains.

As shown in FIG. 8, surrounding the inner ring 124 is a first adhesive portion 126 that is defined by adhesive disposed in an annular recess that surrounds the conductive dome 118. Further surrounding the first adhesive portion 126 is an intermediate ring 128 that is integrally formed with the main body 102, followed by a second adhesive portion 130. The second adhesive portion 130 is defined by adhesive disposed in arcuate recesses arranged concentrically outwardly from the first adhesive portion 126. The second adhesive portion 130 is further bounded or surrounded by an outer ring 132, which is also integrally formed with the main body 102. The first and second adhesive portions 126, 130 serve to securely adhere the main body 102 to the fetal skin, even in the aqueous environment found in the uterus. The adhesive portions 126, 130 may be formed of any adhesive as chosen by a skilled artisan, for example the adhesive may be rubber latex based, acrylate, silicone, or a hydrocolloid based adhesive. Although two adhesive portions 126, 130 are shown, one of ordinary skill in the art may also select any other number of adhesive portions within the scope of the present disclosure.

With continued reference to FIG. 8, the inner ring 124, intermediate ring 128, and outer ring 132 also function to protect the adhesive portions 126, 130 from the amniotic fluid. In particular, radial walls 134 may be intermittently spaced between the intermediate ring 128 and outer ring 132. The radial walls 134 separate the second adhesive portion 130 into separate compartments. The compartments protect the integrity of the second adhesive portion 130 in operation. For example, even if one compartment loses its adhesive properties due to excess moisture or wetness, the excess moisture or wetness does not spread to the adhesive in other compartments due to the placement of the radial walls 134.

Additionally, to further protect the adhesive portions 126, 130 from drying out or being contaminated prior to use, the first side 104 may have a peel-away backing (not shown). Any suitable peel-away backing material that is sterile and suitable for use in medical settings may be employed. In operation, the peel-away backing is removed prior to application of the fetal scalp monitor 100 to the scalp of the fetus 101 in utero.

Although it should be understood that a further vacuum or suction force is not required due to the adhesive portions 126, 130 being sufficient to adhere the fetal scalp monitor 100 to the scalp of the fetus 101, it should also be appreciated that the fetal scalp monitor 100 may be further adapted to adhere to the scalp of the fetus 101 by vacuum or suction force, as desired.

As mentioned hereinabove, the inner ring 124 may be formed from an elastomer suitable for forming a seal with the fetal scalp. Suitable types of elastomers may include medical-grade rubber or silicone. Likewise, the intermediate ring 128 and the outer ring 132 may be made of rubber, silicone, or any other suitable material chosen by skilled artisan. In addition, the flexible backbone 108 may have indents, grooves, or channels formed on the second side 106 that are configured to receive the intermediate ring 128, and outer ring 132. In an alternative embodiment, the intermediate ring 128 and the outer ring 132 may be integrally formed with the flexible backbone 108 of the main body 102, and formed from a same material as the main body 102. It should be understood that other suitable configurations and materials for the flexible backbone 108 of the main body 102, as well as the inner ring 124, the intermediate ring 128, and the outer ring 132, may also be selected by one of ordinary skill in the art within the scope of the present disclosure.

With renewed reference to FIGS. 5-8, the second side 106 may have an insulating layer 136 of greater diameter than the conductive dome 118 to electrically shield the grounding ring 110 from the electrical current of the conductive dome 118. For example, the insulating layer 136 may be a woven polypropylene (e.g., a PROLENE® mesh, commercially available from Ethicon USA, LLC), a non-porous cloth, PVC, or rubber. The grounding ring 110 needs to be insulated from the conductive dome 118, because in certain embodiments the fetal heart rate may be calculated using a differential or voltage between the conductive dome 118 and the grounding ring 110.

Figure 3:
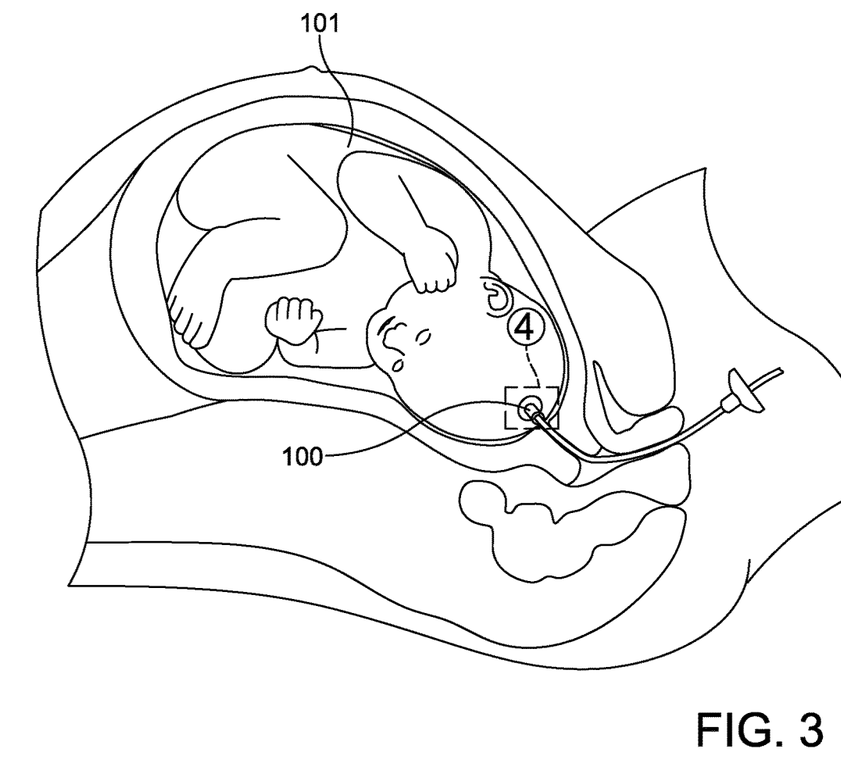
FIG. 3 is an illustration of a fetal scalp monitor according to one embodiment of the present disclosure, and shown attached to the scalp of a fetus in utero.

Additionally, as shown in FIG. 4, the flexible backbone 108 has at least one aperture 138 and the insulating layer 136 has at least one aperture 139. The apertures 138, 139 are configured to receive a plurality of leads 140, e.g., wires or tubes, from the various sensors 118, 120. The leads 140 may be individually connected to the conductive dome 118 and the temperature sensor 120, for example. As shown in FIGS. 3-5, the leads 140 travel through the aperture 139 of the insulating layer 136 and the aperture 138 of the flexible backbone 108 to exit on the first side 104 of the main body 102. Furthermore, these leads 140 may themselves be insulated and may have plugs or connectors 142 that are configured to be placed in communication with fetal monitoring devices (not shown).

It should likewise be appreciated that the grounding ring 110, and tocodynamometer 112 located on the second side 106 of the main body 102, may also have wires 140 that are configured to connect with a fetal monitoring device. The fetal monitoring device may be any device chosen by a skilled artisan, for example, the fetal monitoring device may be a specialized piece of equipment such as a Phillips® Avalon FM50 Fetal Monitor, or may be provided in the form of an application running on a mobile phone, tablet, desktop computer, or the like. Although FIGS. 4-8 show the use of an insulating layer 136, in certain embodiments, there is no need for an insulating layer 136, and the flexible backbone 108 alone may have sufficient insulating properties that are able to protect a shorting of the grounding ring 110 and the conductive dome 118.

In yet another embodiment, the fetal scalp monitor 100 may have a transceiver (not shown) that is connected to the leads 140 and configured to wirelessly transmit data to the fetal monitoring device exterior to the patient. In this example, the fetal scalp monitor 100 is capable of wirelessly communicating with a fetal monitoring device using a variety of methods, including but not limited to Bluetooth®, a wireless local area network, a wireless wide area network, a cellular network, and any other wireless transmission method chosen by a skilled artisan, as desired. It should be appreciated that wirelessly transmitting the data from the various sensors presents certain advantages to the pregnant patient, including comfort and the ability to move more freely.

In operation, when a woman is in labor, the fetal scalp monitor 100 is inserted into the birth canal by a medical professional and is pressed against the scalp of the fetus 101. The adhesive portions 126, 130 function to secure the fetal scalp monitor 100 onto the scalp, despite the presence of fluid in the uterine environment. The fetal scalp monitor 100 then transmits (either wired or wirelessly) information on the vital signs of the fetus 101 and the force of contractions within the uterus to the external fetal monitoring device, to be used by the medical professional in monitoring both the woman and the fetus.

While certain representative embodiments and details have been shown for purposes of illustrating the fetal scalp monitor, it will be apparent to those skilled in the art that various changes may be made without departing from the scope of the disclosure, which is further described in the following appended claims.

What is claimed is:
1. A fetal scalp monitor comprising:
a main body having a first side and a second side;
an electrical ground disposed on the first side of the main body;
a conductive dome disposed on the second side of the main body;
at least one sensor disposed within the conductive dome; and
at least one adhesive disposed on the second side of the main body, the at least one adhesive including a first adhesive portion and a second adhesive portion;
wherein the second side has an inner ring, an intermediate ring, and an outer ring, the first adhesive portion disposed between the inner ring and the intermediate ring, and the second adhesive disposed between the intermediate ring and the outer ring;
wherein the inner ring has a smaller diameter than the intermediate ring and the intermediate ring has a smaller diameter than the outer ring;
wherein the main body has a planar backbone disposed between the first side and the second side of the main body.

2. The fetal scalp monitor of claim 1, wherein the at least one sensor is disposed inside of the conductive dome, and the at least one sensor includes a temperature sensor.

3. The fetal scalp monitor of claim 2, wherein an electrolyte gel is also disposed in the conductive dome and surrounds the temperature sensor.

4. The fetal scalp monitor of claim 3, wherein the inner ring is disposed on a free edge of the conductive dome.

5. The fetal scalp monitor of claim 4, wherein the inner ring is configured to seal the electrolyte gel within the dome when the main body is adhered to skin of a fetus.

6. The fetal scalp monitor of claim 1, wherein the main body has a strap affixed to the first side.

7. The fetal scalp monitor of claim 1, wherein the diameter of the main body is between 1.4 cm and 4.0 cm.

8. The fetal scalp monitor of claim 1, further comprising an insulating layer disposed on the second side of the main body.

9. The fetal scalp monitor of claim 8, wherein the insulating layer has an outer diameter that is greater than an outer diameter of the conducting dome.

10. The fetal scalp monitor of claim 9, wherein the insulating layer is disposed between the conducting dome and the main body.

11. The fetal scalp monitor of claim 1, wherein the first side further has a tocodynamometer.

12. The fetal scalp monitor of claim 11, wherein the tocodynamometer and the electrical ground are each in the shape of a ring and the tocodynamometer is disposed concentrically outside of the electrical ground.

13. The fetal scalp monitor of claim 2, wherein the electrical ground, the conductive dome, and the temperature sensor are each connected to leads for communication with a fetal monitoring device.

14. The fetal electrode of claim 13, where the leads connected to the electrical ground and the temperature sensor include an insulated wire.

15. The fetal scalp monitor of claim 1, wherein a plurality of radial walls connects the intermediate ring and the outer ring, the plurality of radial walls intermittently spaced between the intermediate ring and outer ring and separating the second adhesive portion into separate compartments.

16. A fetal scalp monitor comprising:
a main body having a first side and a second side, the main body having a planar backbone disposed between the first side and the second side;
an electrical ground disposed on the first side of the main body;
a temperature sensor disposed on the second side of the main body,
a conductive dome disposed on the second side main body, wherein the temperature sensor is disposed in the conductive dome, and an electrolyte gel is also disposed in the conductive dome and surrounds the temperature sensor;
an inner ring, an intermediate ring, and an outer ring each disposed on the second side of the main body, the inner ring disposed on a free edge of the conductive dome and configured to seal the electrolyte gel within the dome when the main body is adhered to skin of a fetus, wherein the inner ring has a smaller diameter than the intermediate ring and the intermediate ring has a smaller diameter than the outer ring;
an insulating layer disposed on the second side of the main body, wherein the insulating layer is disposed between the conducting dome and the main body; and
at least one adhesive disposed on the second side of the main body, the adhesive including a first adhesive portion and a second adhesive portion, wherein the first adhesive portion of the adhesive is disposed between the inner ring and the intermediate ring, and wherein the second adhesive portion of the adhesive is disposed between the intermediate ring and the outer ring.

17. A method for monitoring a fetus, comprising:
providing a fetal scalp monitor including a main body having a first side and a second side, the main body having a planar backbone disposed between the first side and the second side, an electrical ground disposed on the first side of the main body, a conductive dome disposed on the second side of the main body, at least one sensor disposed within the conductive dome, and at least one adhesive disposed on the second side of the main body the adhesive including a first adhesive portion and a second adhesive portion, wherein the second side has an inner ring, an intermediate ring, and an outer ring, the first adhesive portion disposed between the inner ring and the intermediate ring, and the second adhesive portion disposed between the intermediate ring and the outer ring, wherein the inner ring has a smaller diameter than the intermediate ring and the intermediate ring has a smaller diameter than the outer ring; and
inserting the device into the birth canal and pressing the main body onto a scalp of the fetus until the main body is adhered to the scalp by the adhesive.

18. The fetal scalp monitor of claim 1, wherein the backbone is fabricated from a member of the group consisting of a polycarbonate, a polyethylene, and a polypropylene.

19. The fetal scalp monitor of claim 1, wherein the second side of the main body includes a grounding ring extending outwardly therefrom.

20. The fetal scalp monitor of claim 12, wherein the tocodynamometer on the first side of the main body is coextensive with the intermediate ring on the second side of the main body.

* * * * *